United States Patent [19]

Evans

[11] 4,203,903

[45] May 20, 1980

[54] PROCESS FOR THE RECOVERY OF SPECTINOMYCIN

[75] Inventor: Timothy W. Evans, Three Rivers, Mich.

[73] Assignee: The Upjohn Company, Kalamazoo, Mich.

[21] Appl. No.: 37,492

[22] Filed: May 10, 1979

[51] Int. Cl.$^2$ .......................................... C07D 319/08
[52] U.S. Cl. .................................................. 260/340.3
[58] Field of Search ..................................... 260/340.3

[56] References Cited

U.S. PATENT DOCUMENTS

| 3,168,533 | 2/1965 | Wiley | 260/340.3 |
| 3,234,092 | 2/1966 | Bergy et al. | 260/340.3 |
| 3,279,989 | 10/1966 | Jahnke | 260/340.3 |
| 3,804,858 | 4/1974 | Meyer | 260/340.3 |

*Primary Examiner*—Ethel G. Love
*Attorney, Agent, or Firm*—Roman Saliwanchik

[57] ABSTRACT

An improved process for recovering the antibiotic spectinomycin from an aqueous concentrate containing the same. This improvement concerns the use of benzoic acid, or a salt thereof, to remove inorganic salts which interfere with the recovery of spectinomycin from an aqueous concentrate.

12 Claims, No Drawings

PROCESS FOR THE RECOVERY OF SPECTINOMYCIN

BACKGROUND OF THE INVENTION

Spectinomycin (formerly known as actinospectacin) is a well-known antibiotic. U.S. Pat. No. 3,234,092 discloses the characteristics of this antibiotic and its production by microbiological means.

A process for recovering spectinomycin from an aqueous solution is disclosed in U.S. Pat. No. 3,804,858. The process disclosed therein removes metal salts from an aqueous solution containing spectinomycin by adjusting the pH of the aqueous solution from about 9.5 to 11. The temperature is held below 20° C., and a solvent selected from the group consisting of acetone, isopropanol, n-propanol and tert butanol is added to precipitate said metal salts.

The process of the subject invention is a clear improvement over the process of U.S. Pat. No. 3,804,858, which is the best prior art process known for removing inorganic salts from an aqueous solution containing spectinomycin.

BRIEF SUMMARY OF THE INVENTION

To an aqueous concentrate containing spectinomycin is added benzoic acid or a salt thereof; the solution is adjusted to a pH of about 5 to about 9; two to two and one-half volumes of a suitable solvent are added; the solution is agitated at a temperature of about 0° to 25° C.; the resulting salt is separated from the liquid; the salt is washed with a suitable solvent containing a salt of benzoic acid and the wash is combined with the liquid of the previous step; and the desired salt of spectinomycin is crystallized by the addition of an appropriate mineral acid.

The subject process leads to a spectinomycin crystalline yield increase of from 15 to 25% as compared with the best prior art process disclosed in U.S. Pat. No. 3,804,858.

DETAILED DESCRIPTION OF THE INVENTION

The subject process for recovering spectinomycin from an aqueous concentrate can be conducted following the sequence of steps as hereinafter set forth. The first step concerns the addition of at least one mole of benzoate per mole of spectinomycin in an aqueous concentrate. Preferably, at least two moles of benzoate are added per mole of spectinomycin. The concentration of spectinomycin in the aqueous concentrate can range from about 50 to about 100 mg/ml. The more concentrated the solution the more efficient is the procedure. With regard to the benzoate, any salt of benzoic acid can be used, as well as benzoic acid itself. Suitable salts include the sodium (preferred), potassium, and calcium.

After the addition of benzoate to the aqueous concentrate, the concentrate is adjusted to a pH of about 5 to about 9 with an alkali, for example, sodium hydroxide. A pH of about 7.5 appears to give the best results.

The next step in the process concerns the addition of a water-miscible solvent to the pH adjusted aqueous concentrate to which the benzoate has been added. The solvent can be acetone (preferred), methanol, ethanol, n-propanol, i-propanol, or t-butanol. The solvent can be added in an amount from about one to ten volumes.

Upon the addition of the solvent to the aqueous concentrate, the concentrate is agitated while the temperature range is maintained between about 0° C. to about 25° C., and preferably at about 0° C. to about 5° C. The agitation is not critical and can vary from a few minutes to three hours with the aim being to see evidence of salt formation in the solution.

Following this period of agitation, a formation of the salt appears and this salt can be separated from the liquid phase. Such filtration can be done, advantageously, by the use of a filter, or by use of centrifugation to give a filtrate containing spectinomycin and being substantially free of inorganic salts.

The salt which is separated from the liquid can be washed with aqueous solvent, as used above, which contains benzoate. The wash can be combined with the liquid from the previous step.

The crystalline salt of spectinomycin can be recovered from the above liquid containing spectinomycin by the addition of an appropriate mineral acid. For example, upon the addition of hydrochloric acid there is obtained crystalline spectinomycin dihydrochloride. Upon the addition of sulfuric acid there is obtained crystalline spectinomycin sulfate.

The sequence of the first three steps of the process as described above can be varied according to the desires of those skilled in the art.

The following examples are illustrative of the process and products of the invention, but are not to be construed as limiting. All percentages are by weight and all solvent mixture proportions are by volume unless otherwise noted.

EXAMPLE 1

SPECTINOMYCIN DIHYDROCHLORIDE

Aqueous concentrate (30 l) containing spectinomycin (82 mg/ml) is cooled to about 0° C. To this concentrate is added 3.3 kg of sodium benzoate and the pH is adjusted to 7.5 with concentrated NaOH. The aqueous concentrate is then added to 75 l of acetone which had been precooled to about 0° C. This solution is agitated for about 10 minutes and the clear liquid is then removed with a well point filter. The pH of this first filtrate is adjusted with hydrochloric acid as soon as possible. The remaining cake from the filtration operation is reslurried in 28 liters of 75% acetone-water plus 0.77 kg of sodium benzoate for about 15 minutes at about 0° C. The clear liquid is then removed as above with a well point filter and combined with the first filtrate. The remaining salt cake is again reslurried with 28 liters of 80% acetone-water for about 15 minutes at about 0° C. Again, the clear liquid is removed with a well point filter and combined with the first filtrate. To the combined filtrate is added concentrated hydrochloric acid to a pH of about 2.0. Also, 25 l of acetone is added. This solution is then agitated for about two hours at a temperature of about 0° C. to 5° C. Crystalline spectinomycin dihydrochloride is removed by filtration upon formation.

EXAMPLE 2

SPECTINOMYCIN SULFATE

By following the procedures of Example 1 but substituting sulfuric acid for hydrochloric acid and adjusting the pH to about 2.5 to 3.0, there is obtained crystalline spectinomycin sulfate.

I claim:

1. A process for recovering spectinomycin from an aqueous concentrate containing spectinomycin and inorganic salts which comprises:
   (a) adding benzoic acid or a salt thereof to said aqueous concentrate;
   (b) adjusting the pH of said concentrate to about 5 to about 9;
   (c) adding a water-miscible solvent to said pH adjusted concentrate;
   (d) agitating and separating salt cake from said concentrate to obtain a filtrate containing spectinomycin; and,
   (e) recovering crystalline spectinomycin salt upon addition of an appropriate mineral acid to said filtrate containing spectinomycin.

2. A process, according to claim 1, wherein sodium benzoate is added to the aqueous concentrate containing spectinomycin.

3. A process, according to claim 1, wherein acetone is added to said pH adjusted concentrate containing spectinomycin.

4. A process for recovering spectinomycin from an aqueous concentrate containing spectinomycin and inorganic salts which comprises:
   (a) adding at least two moles of sodium benzoate per mole of spectinomycin to said aqueous concentrate containing spectinomycin and inorganic salts;
   (b) adjusting the pH of said concentrate to about 7.5 with concentrated NaOH;
   (c) adding acetone to said pH adjusted concentrate;
   (d) agitating and separating salt cake from said concentrate to obtain a filtrate containing spectinomycin and being substantially free of inorganic salts; and,
   (e) recovering crystalline spectinomycin salt upon addition of an appropriate mineral acid to said filtrate containing spectinomycin.

5. A process, according to claim 4, wherein spectinomycin dihydrochloride is obtained by the addition of hydrochloric acid in the final step.

6. A process, according to claim 4, wherein spectinomycin sulfate is obtained by the addition of sulfuric acid in the final step.

7. A process for removing inorganic salts from an aqueous concentrate containing spectinomycin and said inorganic salts which comprises:
   (a) adding benzoic acid or a salt thereof to said aqueous concentrate;
   (b) adjusting the pH of said concentrate to about 5 to about 9;
   (c) adding a water-miscible solvent to said pH adjusted concentrate; and,
   (d) agitating and separating salt cake from said concentrate to obtain a filtrate containing spectinomycin and being substantially free of inorganic salts.

8. A process, according to claim 7, wherein sodium benzoate is added to the aqueous concentrate containing spectinomycin.

9. A process, according to claim 7, wherein acetone is added to said pH adjusted concentrate containing spectinomycin.

10. A process for removing inorganic salts from an aqueous concentrate containing spectinomycin and said inorganic salts which comprises:
    (a) adding at least two moles of sodium benzoate per mole of spectinomycin to said aqueous concentrate containing spectinomycin and inorganic salts;
    (b) adjusting the pH of said concentrate to about 7.5 with concentrated NaOH;
    (c) adding acetone to said pH adjusted concentrate; and,
    (d) agitating and separating salt cake from said concentrate to obtain a filtrate containing spectinomycin and being substantially free of inorganic salts.

11. A process for removing inorganic salts from an aqueous concentrate containing spectinomycin and said inorganic salts which comprises adding benzoic acid or a salt thereof, and a water-miscible solvent to said concentrate adjusted to a pH of about 5 to about 9.

12. A process, according to claim 11, wherein sodium benzoate and acetone are added to said concentrate adjusted to a pH of about 7.5.

* * * * *